United States Patent [19]
Olson et al.

[11] Patent Number: 5,620,465
[45] Date of Patent: Apr. 15, 1997

[54] EXTERNAL DEFIBRILLATOR FOR PRODUCING AND TESTING BIPHASIC WAVEFORMS

[75] Inventors: Kenneth F. Olson, Minneapolis; Byron L. Gilman, Plymouth, both of Minn.

[73] Assignee: SurvivaLink Corporation, Minneapolis, Minn.

[21] Appl. No.: 490,831

[22] Filed: Jun. 8, 1995

[51] Int. Cl.$^6$ ................................................. A61N 1/39
[52] U.S. Cl. ................................................................ 607/5
[58] Field of Search .................................. 607/4, 5, 7, 9, 607/11, 30

[56] References Cited

U.S. PATENT DOCUMENTS

| | | | |
|---|---|---|---|
| 3,706,313 | 12/1972 | Milani et al. | 128/419 D |
| 3,857,398 | 12/1974 | Rubin | 128/419 D |
| 3,886,950 | 6/1975 | Ukkestad et al. | 128/419 D |
| 4,050,004 | 9/1977 | Greatbatch | 363/59 |
| 4,566,457 | 1/1986 | Stemple | 128/419 D |
| 4,619,265 | 10/1986 | Morgan et al. | 607/7 |
| 4,800,883 | 1/1989 | Winstrom | 607/7 |
| 4,823,796 | 4/1989 | Benson | 128/419 D |
| 4,998,531 | 3/1991 | Bocchi et al. | 607/5 |
| 5,199,429 | 4/1993 | Kroll et al. | 607/5 |
| 5,306,291 | 4/1994 | Kroll et al. | 607/5 |
| 5,385,575 | 1/1995 | Adams | 607/15 |
| 5,395,395 | 3/1995 | Hedberg | 607/7 |
| 5,405,361 | 4/1995 | Persson | 607/5 |
| 5,411,525 | 5/1995 | Swanson et al. | 607/5 |

FOREIGN PATENT DOCUMENTS

| | | |
|---|---|---|
| 25894/62 | 12/1962 | Australia . |
| 0445800A1 | 9/1991 | European Pat. Off. . |
| 0487776A1 | 6/1992 | European Pat. Off. . |
| WO94/27674 | 12/1994 | WIPO . |

*Primary Examiner*—William E. Kamm
*Assistant Examiner*—George R. Evanisko
*Attorney, Agent, or Firm*—Patterson & Keough, P.A.

[57] ABSTRACT

An external defibrillator including an operator interface and a high voltage circuit responsive to a controller for producing monophasic waveform defibrillation pulses and/or biphasic waveform defibrillation pulses. The controller can implement a biphasic waveform test protocol by causing the high voltage circuit to sequentially generate one or more biphasic waveform defibrillation pulses before generating monophasic waveform defibrillation pulses in response to sequential actuations of the operator interface during a patient rescue.

10 Claims, 3 Drawing Sheets

EXTERNAL DEFIBRILLATOR FOR PRODUCING AND TESTING BIPHASIC WAVEFORMS

BACKGROUND OF THE INVENTION

1. Field of the Invention

The present invention relates generally to external defibrillators. In particular, the present invention is an automatic external defibrillator for generating and testing biphasic waveforms.

2. Description of the Related Art

Cardiac arrest, exposure to high voltage power lines and other trauma to the body can result in heart fibrillation, the rapid and uncoordinated contraction of the cardiac muscle. The use of external defibrillators to restore the heartbeat to its normal pace through the application of an electrical shock is a well recognized and important tool for resuscitating the patients.

Commercially available defibrillators such as those available from Surviva Link Corporation, the assignee of the present application, are configured to produce monophasic waveform defibrillation pulses. Monophasic (i.e., single polarity) pulses such as the Lown waveform and the truncated exponential waveform have been demonstrated to be effective for defibrillation, and meet standards promulgated by the Association for Advancement of Medical Instrumentation (AAMI). Electrical circuits for producing monophasic waveform defibrillation pulses are generally known and disclosed, for example, in the Persson U.S. Pat. No. 5,405,361.

The efficacy of biphasic waveform pulses (actually two successive pulses of opposite polarities) has been established for implantable defibrillators. For example, studies conducted on implantable defibrillators have shown that biphasic waveform defibrillation pulses result in a lower defibrillation threshold than monophasic pulses. A variety of theories have been proposed to explain the defibrillation characteristics of biphasic waveform pulses.

It is anticipated that the efficacy and advantages of biphasic waveform pulses that have been demonstrated in implantable defibrillators will be demonstrated in external defibrillators as well. However, because of the difficulties involved in testing external defibrillators, the efficacy of biphasic waveform pulses produced by these instruments has not yet been fully studied. External defibrillation is typically used in emergency settings in which the patient is either unconscious or otherwise unable to communicate. It is therefor difficult if not impossible to obtain informed consent from the patient for such tests. Time is also of the essence since studies have shown that the chances for successful resuscitation diminish approximately ten percent per minute. The use of experimental defibrillation pulses must therefor be completed quickly. The capability of quickly switching to a proven defibrillation pulse following an unsuccessful rescue with the experimental pulse must also exist. For these reasons it is evident that there is a need for external defibrillators and protocols capable of producing and testing biphasic waveform pulses.

SUMMARY OF THE INVENTION

One embodiment of the present invention is an external defibrillator high voltage circuit for generating monophasic and/or biphasic waveform defibrillation pulses. The high voltage circuit includes first and second output terminals configured for electrical interconnection to electrodes, a supply terminal configured for electrical interconnection to a charge voltage potential, and two or more capacitors for storing electrical energy. Charge circuitry is responsive to charge control signals, and electrically interconnects each of the capacitors to the supply terminal to charge the capacitors to the charge voltage potential. Pulse initiating circuitry is responsive to first and second polarity pulse control signals. The pulse initiating circuitry can electrically interconnect one or more of the capacitors in a series circuit and with a first electrical polarity orientation between the first and second output terminals to produce a first polarity pulse in response to the first polarity pulse control signals, and electrically interconnect one or more of the capacitors in a series circuit and with a second and opposite electrical polarity orientation between the first and second output terminals to produce a second polarity pulse in response to the second polarity pulse control signals.

Another embodiment of the invention includes a controller coupled to the high voltage circuit for producing the pulse control signals, and an operator interface coupled to the controller for causing the controller to initiate the generation of defibrillation pulses. The controller is programmed to implement a biphasic waveform test protocol which causes the high voltage circuit to sequentially generate one or more biphasic waveform defibrillation pulses before generating monophasic waveform defibrillation pulses in response to sequential actuations of the operator interface during a patient rescue.

DETAILED DESCRIPTION OF THE PREFERRED EMBODIMENTS

Figure 1:
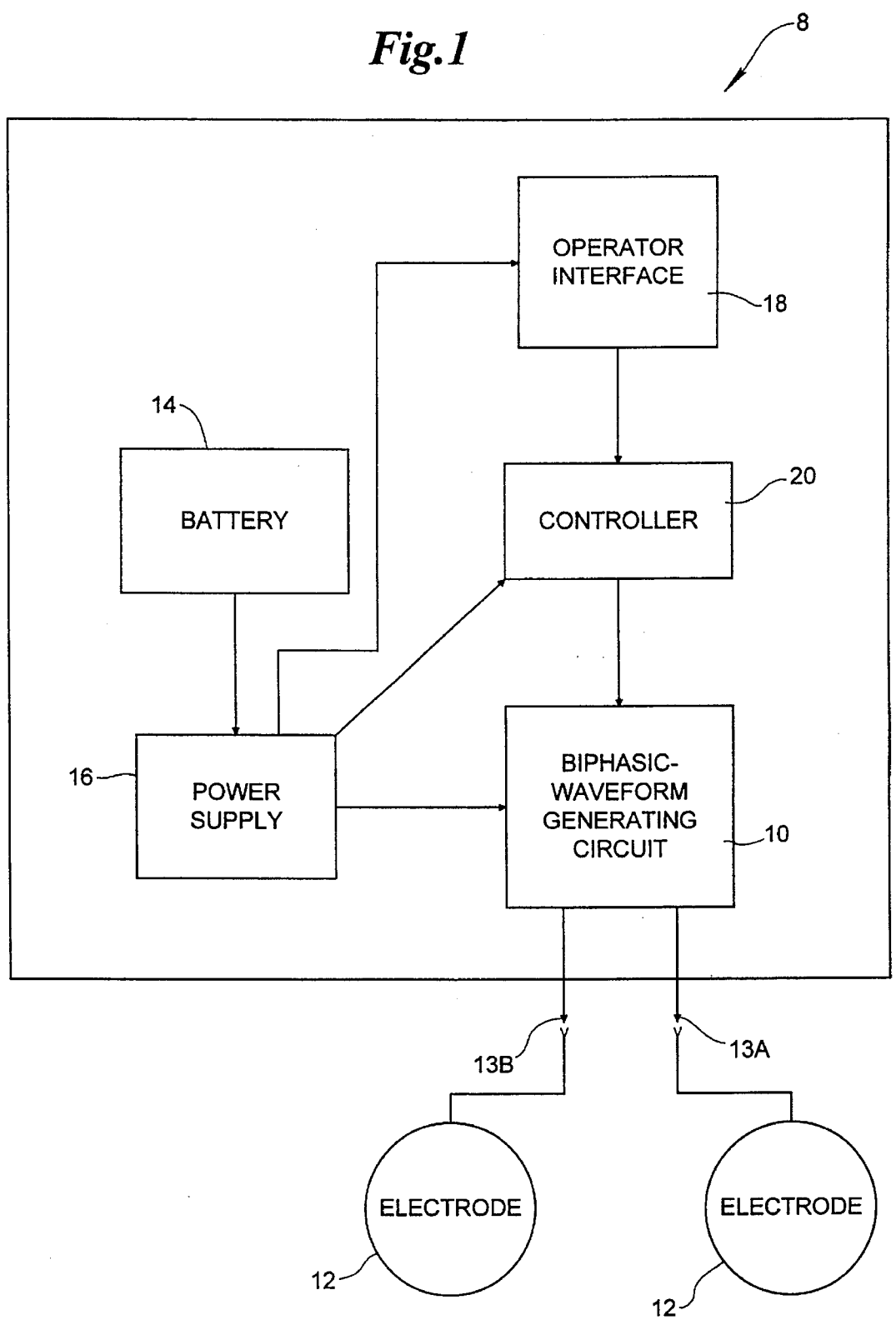
FIG. 1 is a block diagram of a defibrillator in accordance with the present invention.

A portable automatic external defibrillator (AED) 8 which includes a high voltage waveform generating circuit 10 and controller 20 in accordance with the present invention is illustrated generally in FIG. 1. As shown, defibrillator 8 is configured for electrical interconnection to a pair of patient electrodes 12 through connectors 13A and 13B, and also includes rechargeable battery 14, power supply 16 and operator interface 18. Power supply 16 is connected to battery 14 and includes a conventional charging circuit (not separately shown) which provides a regulated charging potential (e.g., 330 volts in one embodiment) to high voltage circuit 10. Power supply 16 is also connected to provide regulated operating potentials (e.g., ±5 volts) to operator interface 18 and controller 20. Controller 20 includes a programmed microprocessor (not separately shown) which is connected to both operator interface 18 and high voltage circuit 10. Operator interface 18 includes one or more control switches (not separately shown) actuated by paramedics or other technicians using defibrillator 8 to resuscitate a patient, as well as visual and/or audible displays (also not shown) which provide information on the operational status of the defibrillator. In response to operator actuation of interface 18, controller 20 causes high voltage circuit 10 to generate biphasic or monophasic defibrillation pulses which are delivered to the patient through electrodes 12. Controller 20 can also be programmed to implement a biphasic waveform pulse test protocol by causing high voltage circuit 10 to generate both monophasic and biphasic waveform pulses. With the exception of high voltage waveform generating circuit 10 and the manner by which the high voltage circuit is controlled by controller 20, defibrillator 8 can be of any conventional or otherwise known design. High voltage circuit 10 and the features of controller 20 described below can, for example, be incorporated into the VIVAlink portable external defibrillator which is commercially available from Surviva Link Corporation of Minnetonka, Minn.

Figure 2:
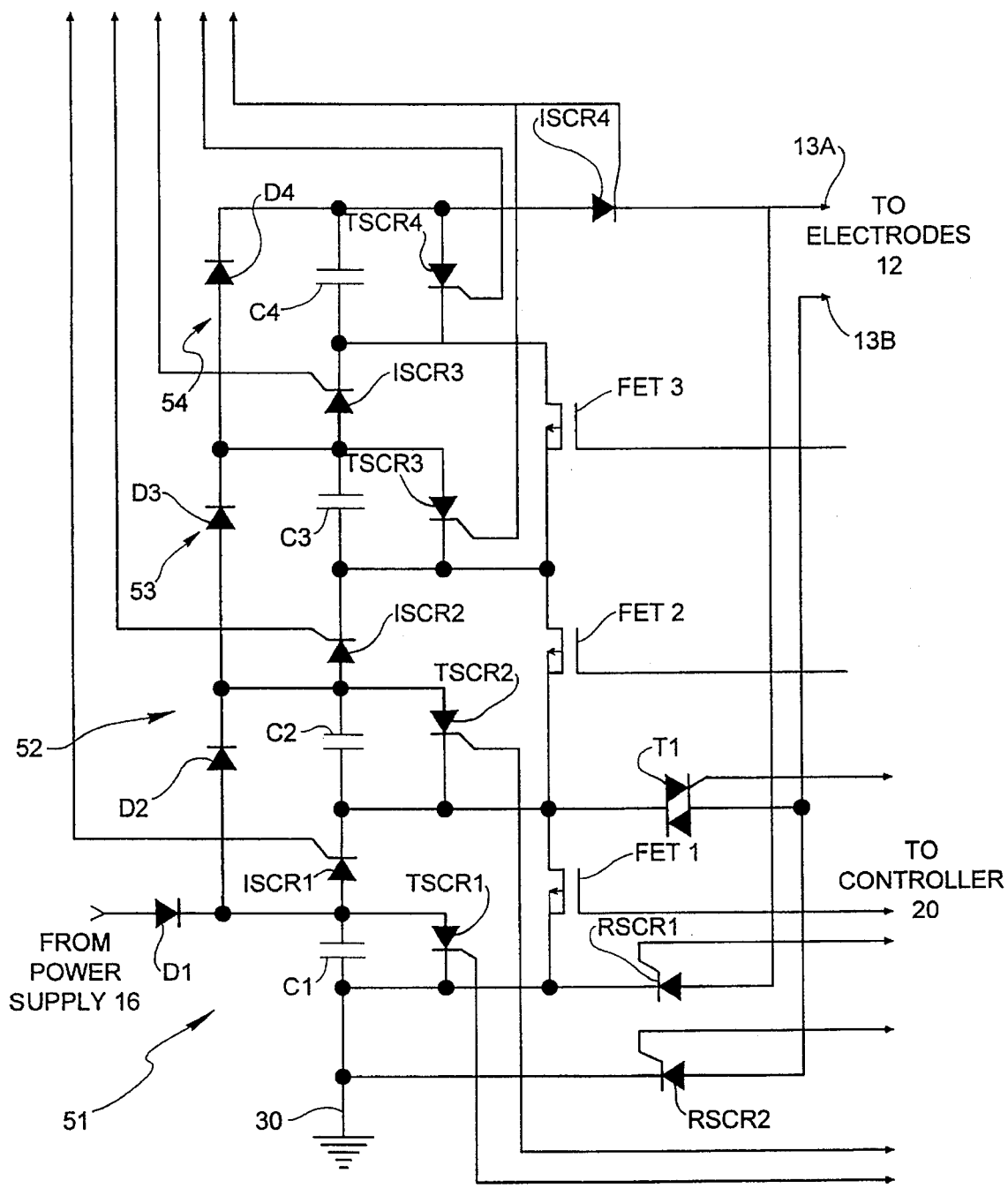
FIG. 2 is a schematic diagram of the high voltage waveform generating circuit shown in FIG. 1.

High voltage waveform generating circuit 10 can be described in greater detail with reference to FIG. 2. In the embodiment shown, high voltage circuit 10 includes four independently controllable charge stages S1–S4 connected between power supply 16, electrode terminals 13A and 13B and reference or reference terminal 30. First stage S1 includes capacitor C1, pulse initiating silicon controlled rectifier (SCR) ISCR1 and waveform truncating silicon controlled rectifier TSCR1. A first terminal of capacitor C1 is connected to reference terminal 30, while a second terminal of the capacitor is connected to the anode of initiating rectifier ISCR1. Truncating rectifier TSCR1 is connected in parallel with capacitor C1, and has its cathode and anode connected to the first and second terminals, respectively, of the capacitor. Second stage S2 includes capacitor C2 having a first terminal connected to the cathode of first stage rectifier ISCR1, and rectifiers ISCR2 and TSCR2 which are interconnected to the capacitor in a manner identical to the corresponding circuit elements of stage S1. Third stage S3 includes capacitor C3 and rectifiers ISCR3 and TSCR3 interconnected to each other and to the preceding stage S2 in a manner identical to the corresponding circuit elements of stage S2. Similarly, stage S4 includes capacitor C4 and rectifiers ISCR4 and TSCR4 interconnected to each other and to the preceding stage S3 in a manner identical to the corresponding circuit elements of stage S3. The cathode of initiating rectifier ISCR4 is connected to electrode terminal 13A. The gates of initiating rectifiers ISCR1–ISCR4 and truncating rectifiers TSCR1–TSCR4 can be connected to controller 20 through conventional isolation circuits (not shown) such as those shown in the commonly assigned Persson U.S. Pat. No. 5,405,361.

Diodes D1–D4 are interconnected to one another in a series arrangement with the anode of diode D1 connected to power supply 16. As shown, the cathodes of diode D1–D4 are connected to the anodes of the pulse initiating rectifiers ISCR1–ISCR4 of each stage S1–S4, respectively. Charge control field effect transistors FET1–FET3 have channels interconnected to one another in a series arrangement to reference terminal 30. This circuit arrangement enables the use of lower voltage transistors FET1–FET3. The source terminals of FET1–FET3 are connected to the cathodes of initiating rectifiers ISCR1–ISCR3, respectively. The gates of transistors FET1–FET3 are connected to controller 20. Again, isolation circuits such as those shown in the Persson U.S. Pat. No. 5,405,361 can be used to couple the gates of FET1–FET3 to controller 20 to help protect the transistors.

Electrode terminals 13A and 13B are connected to reference terminal 30 by ground reference silicon controlled rectifiers RSCR1 and RSCR2, respectively. The anodes of rectifiers RSCR1 and RSCR2 are connected to electrode terminals 13A and 13B, respectively, while the cathodes of the rectifiers are connected to reference terminal 30. A biphasic control triac T1 is connected between the cathode of rectifier ISCR1 (i.e., to a node between two capacitors C1–C4) and electrode terminal 13B. Although not shown, a pair of back-to-back silicon controlled rectifiers having gates connected to controller 20 can be substituted for triac T1. The gates of rectifiers RSCR1 and RSCR2 and triac T1 are individually coupled to controller 20 through isolation circuits (not shown) such as those described above. Rectifiers ISCR1–ISCR4, TSCR1–TSCR4, RSCR1, RSCR2, triac T1 and transistors FET1–FET3 all function as electronic switches and are controlled by gate control signals from controller 20 (i.e., are switched between electrically "on" and "off" states) to control the generation of defibrillation pulses that are applied to electrodes 12 through terminals 13A and 13B. In particular, controller 20 is programmed to switch the rectifiers, triac and transistors in such a manner as to i) charge capacitors C1–C4 and ii) discharge the capacitors in such a manner as to produce defibrillation pulses having a) a biphasic waveform, and/or b) a monophasic waveform.

Capacitors C1–C4 are charged by switching off all rectifiers ISCR1–ISCR4, TSCR1–TSCR4, RSCR1, and RSCR2, and triac T1, while simultaneously switching on transistors FET1–FET3. The first terminal of each capacitor C1–C4 is thereby connected to reference terminal 30 while the charging voltage from power supply 16 is applied to the second terminal of each capacitor through diodes D1–D4, respectively. Capacitors C1–C4 are thereby each charged to the charging voltage with respect to ground (i.e., in parallel). Transistors FET1–FET3 are switched off after the capacitors C1–C4 are fully charged, and rectifiers ISCR1–ISCR4, TSCR1–TSCR4, RSCR1, and RSCR2, and triac T1 held off to maintain high voltage circuit 10 in a charged and discharge-ready state.

Figure 3:
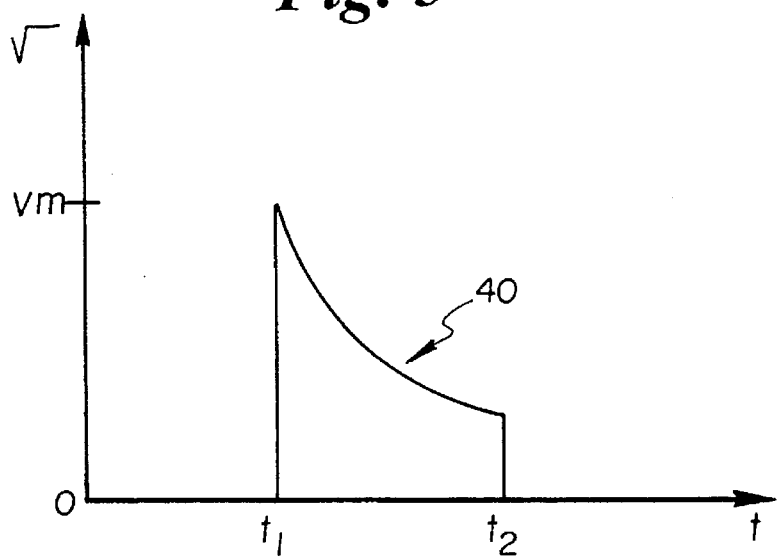
FIG. 3 is a diagram of a truncated exponential monophasic waveform defibrillation pulse produced by the defibrillator shown in FIG. 1.

FIG. 3 is an illustration of a truncated exponential monophasic waveform defibrillation pulse 40 produced by high voltage circuit 10. To produce the monophasic waveform pulse 40, controller 20 switches on rectifiers ISCR1–ISCR4 and RSCR2 at time $t_1$, and switches on rectifiers TSCR1–TSCR4 at time $t_2$. At time $t_1$ capacitors C1–C4 are therefore interconnected in series between electrode terminals 13A and 13B in a first polarity orientation, and terminal 13B referenced to reference terminal 30. Switching on the rectifiers TSCR1–TSCR4 at time $t_2$ causes each of the capacitors C1–C4 to discharge through the respective rectifier and thereby truncate the defibrillation pulse. The total energy delivered to the patient by the monophasic waveform pulse 40 is controlled by peak potential $V_m$ and the length of time between the initiation and termination of the pulse (i.e., $t_2-t_1$). The magnitude of the peak potential $V_m$ is determined by the number of charged capacitors C1–C4 that are connected in series between electrode terminals 13A and 13B (i.e., the number (N) of stages in circuit 10) and the charge voltage to which each of the capacitors is charged by power supply 16. Following the delivery of the monophasic waveform defibrillation pulse 40, high voltage circuit 10 is recharged in the manner described above.

Figure 4:
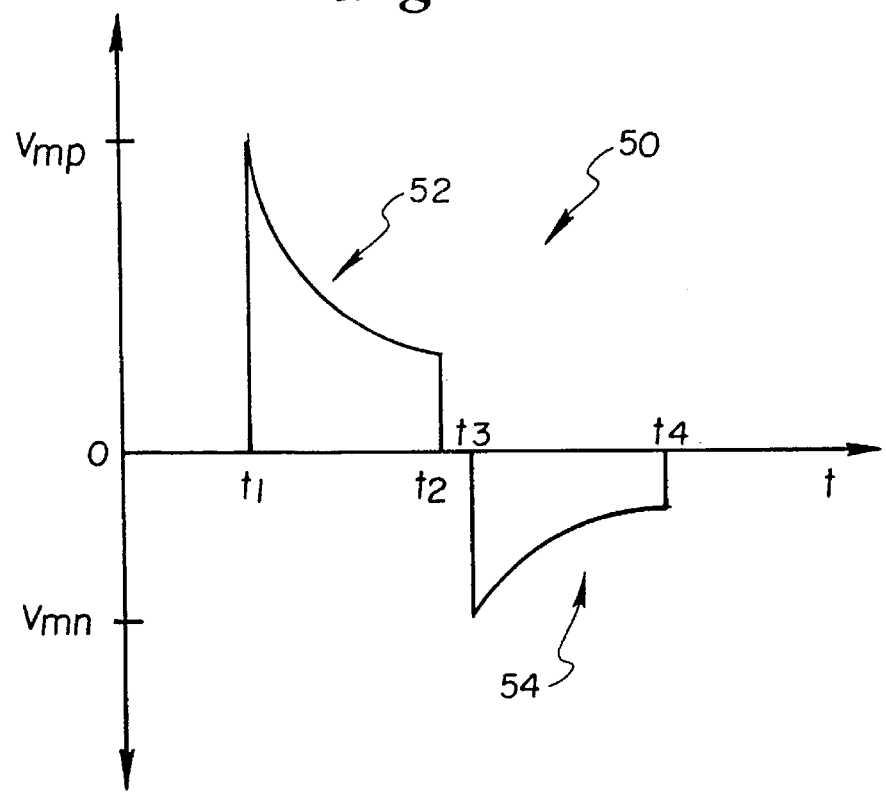
FIG. 4 is a diagram of a biphasic waveform defibrillation pulse produced by the defibrillator shown in FIG. 1.

FIG. 4 is an illustration of a biphasic waveform defibrillation pulse 50 produced by high voltage circuit 10. As shown, pulse 50 includes both a positive polarity component 52 and a negative polarity component 54. To produce positive polarity component 52 of pulse 50, controller 20 switches on rectifiers ISCR2–ISCR4 and triac T1 at time $t_1$, and switches on rectifiers TSCR2–TSCR4 at time $t_2$. After a short delay, negative polarity component 54 is produced when controller 20 switches on rectifiers ISCR1, RSCR1 and triac T1 at time $t_3$, and switches on rectifier TSCR1 at time t4. At time $t_1$ capacitors C2–C4 are therefore interconnected in series between electrode terminals 13A and 13B in a first polarity orientation. The positive peak potential $V_{mp}$ applied to terminals 13A and 13B is therefore equal to the sum of the potential to which capacitors C2–C4 are charged (i.e., three times the charge voltage provided by power supply 16 in the embodiment shown in FIG. 2). Switching on the rectifiers TSCR2–TSCR4 at time $t_2$ causes each of the capacitors C2–C4 to discharge through the respective rectifier and thereby truncate the positive polarity portion 52 of defibrillation pulse 50. The total energy delivered to the patient by the portion 52 of pulse 50 is controlled by peak potential $V_{mp}$ and the length of time between the initiation and termination of the pulse portion (i.e., $t_2-t_1$). The magnitude of the peak potential $V_{mp}$ is determined by the number of charged capacitors (e.g., C2–C4) that are connected in series between electrode terminals 13A and 13B (i.e., the number of stages in circuit 10 between triac T1 and terminal 13A) and the charge voltage to which each of the capacitors is charged by power supply 16.

At time $t_3$ capacitor C1 is interconnected between electrode terminals 13A and 13B in a second polarity orientation, and terminal 13A referenced to reference terminal 30. The negative peak potential $V_{mn}$ applied to terminals 13A and 13B is therefore equal to the charge on capacitor C1. Switching on the rectifier TSCR1 at time $t_4$ causes capacitor C1 to discharge through the rectifier and thereby truncate the negative polarity portion 54 of defibrillation pulse 50. The total energy delivered to the patient by the portion 54 of pulse 50 is controlled by peak potential $V_{mn}$ and the length of time between the initiation and termination of the pulse portion (i.e., $t_4-t_3$). The magnitude of the peak potential $V_{mn}$ is determined by the number of charged capacitors that are connected in series between electrode terminals 13A and 13B (i.e., the number of stages in circuit 10 between triac T1 and reference terminal 30) and the charge voltage to which each of the capacitors is charged by power supply 16. In the embodiment shown in FIG. 2, the positive peak potential $V_{mp}$ of the positive polarity component 52 is three times the negative peak potential $V_{mn}$ of the negative polarity component 54. Following the delivery of the defibrillation pulse 50, high voltage circuit 10 is recharged in the manner described above.

Controller 20 can be programmed to cause high voltage circuit 10 to deliver monophasic waveform pulses such as 40 or biphasic waveform pulses such as 50 in response to operator actuation of defibrillator 8 through interface 18. Furthermore, if the operating program for controller 20 is stored in replaceable or reprogrammable memory (not separately shown in FIG. 1), the defibrillator can be conveniently and efficiently reconfigured following its original manufacture to provide a different type of waveform pulse. For example, if defibrillator 8 is originally configured to generate monophasic pulses such as 40, the defibrillator can be reconfigured in the field to generate biphasic pulses such as 50 if the efficacy or desirability of biphasic pulses is determined to be superior to those of monophasic pulses. Defibrillator 8 is therefor forwardly compatible, and the owner can have the instrument upgraded without incurring the expense of a new instrument.

Controller 20 can also be programmed to cause high voltage circuit 10 to alternate between the delivery of monophasic waveform pulses 40 and biphasic waveform pulses 50 during each use of defibrillator 8. For example, controller 20 can be programmed in such a manner that after defibrillator 8 is set up for patient rescue (e.g., after electrodes 12 are positioned on a patient), biphasic waveform pulses 50 are delivered in response to the first or first and second (i.e., one or more) actuations of interface 18, and monophasic waveform pulses 40 are delivered in response to subsequent actuations of the interface. If the first or first and second rescue attempts using biphasic waveform pulses 50 are unsuccessful at resuscitating the patient, monophasic waveform pulses 40 will be delivered for subsequent rescue attempts. The operator need not make any decisions or actuate interface 18 to switch between waveforms since this protocol is programmed into controller 20 and therefore transparent to the operator. Blinded studies of the efficacy of different waveforms can therefor be performed without having to switch defibrillators during a patient rescue.

Although the present invention has been described with reference to preferred embodiments, those skilled in the art will recognize that changes can be made in form and detail without departing from the spirit and scope of the invention.

What is claimed is:

1. An external defibrillator device for testing the efficacy of biphasic waveform defibrillation pulses including:

a power supply;

pulse generating circuitry coupled to the power supply for generating monophasic waveform and biphasic waveform defibrillation pulses;

an interface actuated by an operator during patient rescues; and control means for controlling the operation of the pulse generating circuitry wherein the control means is coupled to the pulse generating circuitry and the interface, and wherein the control means causes the pulse generating circuitry to sequentially generate at least one biphasic waveform defibrillation pulse before generating monophasic waveform defibrillation pulses in response to sequential actuations of the interface during a patient rescue.

2. An external defibrillator device including a capacitive-discharge generating circuitry having means for creating biphasic and monophasic waveforms from said capacitive-discharge wherein the structure of the waveforms is determined by a prompting means operating on the circuitry and said prompting means being integrated with an operator interface, the circuitry comprising:

a power supply;

first and second output terminals for electrical interconnection to a plurality of electrodes for introducing said capacitive-discharge into a cardiac patient;

a supply terminal and a reference terminal electrically connected to the power supply;

at least two capacitors for storing said capacitive-discharge;

charge circuitry for generating defibrillation waveforms, wherein the charge circuitry is electrically connected to the supply and reference terminals and the at least two capacitors;

control means for controlling the operation of the charge circuitry wherein the control means generates first and second polarity pulse control signals for generating monophasic defibrillation waveforms in response to actuation of the operator interface; and pulse initiating circuitry electrically connected to the control means wherein the pulse initiating circuitry electrically interconnects one or more of the capacitors in a series circuit and with a first electrical polarity orientation between the first and second output terminals to produce a first polarity pulse in response to the first polarity pulse control signals, and for electrically interconnecting one or more of the capacitors in a series circuit and with a second opposite electrical polarity orientation between the first and second output terminals to produce a second polarity pulse in response to the second polarity pulse control signals.

3. A high voltage circuit implemented in an external defibrillator device to produce a capacitive-discharge comprising one of discrete series and sequential combinations of biphasic and monophasic waveform defibrillation pulses, the external defibrillator device comprising:

a power supply;

circuit means coupled to the power supply for generating monophasic and biphasic waveform defibrillation pulses;

control means for controlling the operation of the high voltage circuitry in electrical communications with the circuit means; and an actuating operator interface coupled to the control means for causing the control means to initiate generation of the defibrillation pulses by the circuit means;

said control means including a programmable protocol means for causing the circuit means to sequentially generate at least one of the biphasic defibrillation pulses before generating the monophasic waveform defibrillation pulses in response to sequential actuation of said operator interface during a patient rescue.

4. The circuit of claim 3 further comprising a plurality of output terminals in electrical communication with said biphasic waveform generating circuit.

5. The circuit of claim 4 wherein said plurality of output terminals include connections to a plurality of electrodes through which said defibrillation pulses are introduced into a cardiac patient.

6. The circuit of claim 5 further comprising a reference terminal, and wherein a plurality of independently controllable charge stages are connected between the power supply, said plurality of electrodes and the reference terminal.

7. An external defibrillator device including a system for testing the efficacy of at least one biphasic defibrillation waveform the system having means to switch over to monophasic defibrillation waveform simultaneous with a time when the waveforms are being introduced into a cardiac patient, the system for testing further comprising:

a power supply;

capacitive-discharge generating circuit means in electrical communications with said power supply;

means for creating monophasic and biphasic waveforms;

operator interface means to initiate the discharge; and control means for controlling the operation of the means for creating monophasic and biphasic waveforms in communication with said means for creating the monophasic and biphasic waveforms and coupled to said circuit means;

said interface means having means for prompting said circuit means to operate on said means for creating the monophasic and biphasic waveforms such that at least one biphasic waveform is discharged before switching over to the monophasic waveforms during the discharge time.

8. The device according to claim 7 wherein said means for creating monophasic and biphasic waveforms includes a plurality of capacitors and wherein the operator interface includes initiating circuitry wherein the initiating circuitry configures at least one of the plurality of capacitors such that a first polarity signal is obtained and wherein the initiating circuitry configures at least one of the plurality of capacitors such that a second polarity signal is obtained.

9. The device according to claim 8 wherein said first and second polarity signals comprise said biphasic and monophasic waveforms.

10. The device according to claim 8 further comprising at least one truncating semiconductor switch which includes terminals for receiving said first and second polarity signals to thereby form a parallel electrical connection with said plurality of capacitors and to discharge said capacitors upon receipt of said signals.

* * * * *

UNITED STATES PATENT AND TRADEMARK OFFICE
CERTIFICATE OF CORRECTION

PATENT NO. : 5,620,465
DATED : April 15, 1997
INVENTOR(S) : Kenneth F. Olson

It is certified that error appears in the above-indentified patent and that said Letters Patent is hereby corrected as shown below:

Column 2, line 47, please insert the phrase "multi-phasic or biphasic" after the word "voltage".

Column 6, line 62, please insert the phrase "and biphasic" between the words "monophasic" and "defibrillation".

Signed and Sealed this

Fifth Day of August, 1997

*Attest:*

BRUCE LEHMAN

*Attesting Officer*     *Commissioner of Patents and Trademarks*